(12) United States Patent
Castaneda et al.

(10) Patent No.: US 8,545,540 B2
(45) Date of Patent: Oct. 1, 2013

(54) BONE PLATE WITH PRE-ASSEMBLED DRILL GUIDE TIPS

(75) Inventors: Javier E. Castaneda, Miami, FL (US); Jorge L. Orbay, Coral Gables, FL (US); William F. Doyle, New York, NY (US)

(73) Assignee: Biomet C.V., Gibraltar (GI)

( * ) Notice: Subject to any disclaimer, the term of this patent is extended or adjusted under 35 U.S.C. 154(b) by 174 days.

(21) Appl. No.: 12/977,729

(22) Filed: Dec. 23, 2010

(65) Prior Publication Data
US 2011/0172669 A1 Jul. 14, 2011

Related U.S. Application Data

(63) Continuation of application No. 11/011,917, filed on Dec. 14, 2004, now Pat. No. 8,172,886.

(51) Int. Cl.
*A61B 17/88* (2006.01)

(52) U.S. Cl.
USPC ......................................................... 606/291

(58) Field of Classification Search
USPC .................. 606/280, 281–299, 70, 71, 86 R, 606/96–98; 408/72 B, 115 B, 202, 204, 241 B, 408/241 G; 433/72–76
See application file for complete search history.

(56) References Cited

U.S. PATENT DOCUMENTS

| | | |
|---|---|---|
| 1,105,105 A | 7/1914 | Sherman |
| 1,326,907 A | 1/1920 | Bond |
| 2,406,832 A | 9/1946 | Hardinge |
| 2,443,363 A | 6/1948 | Townsend et al. |
| 2,494,229 A | 1/1950 | Collison |
| 2,500,370 A | 3/1950 | McKibbin |
| 3,289,290 A | 12/1966 | Sandor |
| 3,673,378 A | 6/1972 | Kesling |
| 3,713,221 A | 1/1973 | Malmin |
| 3,741,205 A | 6/1973 | Markilf et al. |
| 3,824,834 A | 7/1974 | Durham |
| 3,842,825 A | 10/1974 | Wagner |
| 3,874,808 A | 4/1975 | Zaccardelli et al. |
| 4,304,117 A | 12/1981 | Rawson |
| 4,364,382 A | 12/1982 | Mennen |
| 4,493,317 A | 1/1985 | Klaue |
| 4,565,193 A | 1/1986 | Streli |
| 4,683,878 A | 8/1987 | Carter |
| 4,740,117 A | 4/1988 | Schaff Deleury et al. |
| 4,867,144 A | 9/1989 | Karas et al. |

(Continued)

FOREIGN PATENT DOCUMENTS

| | | |
|---|---|---|
| AU | 20027914 | 3/2001 |
| CH | 373516 | 11/1963 |

(Continued)

OTHER PUBLICATIONS

The Titanium Distal Radius Plate Technique Guide; Synthes, 1996.

(Continued)

*Primary Examiner* — Mary Hoffman
*Assistant Examiner* — Tara Carter
(74) *Attorney, Agent, or Firm* — Gordon & Jacobson, PC (57) ABSTRACT

Removable drill guide tips are pre-assembled into threaded holes of a bone plate. The tips may be used with an extension to together function as a conventional drill guide. After drilling, the extension or another tool is used to remove the tips from the plate. According to another use, the tip is used as a guide for a drill bit without any additional extension and then removed with a tool.

23 Claims, 6 Drawing Sheets

(56) References Cited

U.S. PATENT DOCUMENTS

| | | |
|---|---|---|
| 4,889,110 A | 12/1989 | Galline et al. |
| 4,905,680 A | 3/1990 | Tunc |
| 4,955,886 A | 9/1990 | Pawluk |
| 4,957,497 A | 9/1990 | Hoogland et al. |
| 5,002,544 A | 3/1991 | Klaue et al. |
| 5,015,248 A | 5/1991 | Burstein et al. |
| 5,022,277 A | 6/1991 | Shaffer |
| 5,053,036 A | 10/1991 | Perren et al. |
| 5,139,497 A | 8/1992 | Tilghman et al. |
| 5,151,103 A | 9/1992 | Tepic et al. |
| 5,161,404 A | 11/1992 | Hayes |
| 5,190,544 A | 3/1993 | Chapman et al. |
| 5,197,966 A | 3/1993 | Sommerkamp |
| 5,201,737 A | 4/1993 | Leibinger et al. |
| 5,269,784 A | 12/1993 | Mast |
| 5,290,288 A | 3/1994 | Vignaud et al. |
| 5,304,180 A | 4/1994 | Slocum |
| 5,336,224 A | 8/1994 | Selman |
| 5,360,448 A | 11/1994 | Thramann |
| 5,364,398 A | 11/1994 | Chapman et al. |
| 5,366,326 A | 11/1994 | Converse |
| 5,372,598 A | 12/1994 | Luhr et al. |
| 5,413,577 A | 5/1995 | Pollock |
| 5,423,826 A | 6/1995 | Coates et al. |
| 5,474,553 A | 12/1995 | Baumgart |
| 5,487,743 A | 1/1996 | Laurain et al. |
| 5,507,801 A | 4/1996 | Gisin et al. |
| 5,509,933 A | 4/1996 | Davidson et al. |
| 5,558,674 A | 9/1996 | Heggeness et al. |
| 5,564,302 A | 10/1996 | Watrous |
| 5,578,036 A | 11/1996 | Stone et al. |
| 5,586,985 A | 12/1996 | Putnam et al. |
| 5,601,553 A | 2/1997 | Trebing et al. |
| 5,634,927 A | 6/1997 | Houston et al. |
| D383,841 S | 9/1997 | Runciman |
| 5,693,055 A | 12/1997 | Zahiri et al. |
| 5,718,705 A | 2/1998 | Sammarco |
| 5,746,742 A | 5/1998 | Runciman et al. |
| 5,752,958 A | 5/1998 | Wellisz |
| 5,779,706 A | 7/1998 | Tschakaloff |
| 5,785,712 A | 7/1998 | Runciman et al. |
| 5,807,396 A | 9/1998 | Raveh |
| 5,851,207 A | 12/1998 | Cesarone |
| 5,888,034 A | 3/1999 | Greenberg |
| 5,935,128 A | 8/1999 | Carter et al. |
| 5,954,722 A | 9/1999 | Bono |
| 5,984,925 A | 11/1999 | Apgar |
| 5,993,449 A | 11/1999 | Schlapher et al. |
| 6,001,099 A | 12/1999 | Huebner |
| 6,007,535 A | 12/1999 | Rayhack et al. |
| 6,066,142 A | 5/2000 | Serbousek et al. |
| 6,077,271 A | 6/2000 | Huebner et al. |
| 6,123,709 A | 9/2000 | Jones |
| 6,129,730 A | 10/2000 | Bono et al. |
| 6,162,243 A | 12/2000 | Gray et al. |
| 6,162,253 A | 12/2000 | Conzemius et al. |
| 6,170,803 B1 | 1/2001 | Liberfarb |
| 6,193,721 B1 | 2/2001 | Michelson |
| 6,235,034 B1 | 5/2001 | Bray |
| 6,283,973 B1 | 9/2001 | Hubbard et al. |
| 6,306,139 B1 | 10/2001 | Fuentes |
| 6,306,171 B1 | 10/2001 | Conzemius |
| 6,325,803 B1 | 12/2001 | Schumacher et al. |
| 6,332,887 B1 | 12/2001 | Knox |
| 6,348,052 B1 | 2/2002 | Sammarco |
| 6,358,250 B1 | 3/2002 | Orbay |
| 6,364,881 B1 | 4/2002 | Apgar et al. |
| 6,364,882 B1 | 4/2002 | Orbay |
| 6,416,518 B1 | 7/2002 | DeMayo |
| 6,436,103 B1 | 8/2002 | Suddaby |
| 6,506,191 B1 | 1/2003 | Joos |
| 6,587,750 B2 | 7/2003 | Gerbi et al. |
| 6,602,255 B1 | 8/2003 | Campbell et al. |
| 6,623,486 B1 | 9/2003 | Weaver et al. |
| 6,656,181 B2 | 12/2003 | Dixon et al. |
| 6,663,632 B1 | 12/2003 | Frigg |
| 6,695,845 B2 | 2/2004 | Dixon et al. |
| 6,712,818 B1 | 3/2004 | Michelson |
| 6,730,091 B1 | 5/2004 | Pfefferle et al. |
| 6,821,278 B2 | 11/2004 | Frigg et al. |
| 6,866,665 B2 | 3/2005 | Orbay |
| 6,928,733 B2 | 8/2005 | Rubbert et al. |
| 6,960,211 B1 | 11/2005 | Pfefferle et al. |
| 7,048,477 B2 | 5/2006 | Abrams |
| 7,128,744 B2 | 10/2006 | Weaver et al. |
| 7,179,260 B2 | 2/2007 | Gerlach et al. |
| 7,229,446 B2 | 6/2007 | Capanni |
| 7,273,481 B2 | 9/2007 | Lombardo et al. |
| 7,357,804 B2 | 4/2008 | Binder et al. |
| 7,473,257 B2 | 1/2009 | Knopfle et al. |
| 7,578,825 B2 | 8/2009 | Huebner |
| 7,740,634 B2 | 6/2010 | Orbay et al. |
| 7,771,433 B2 | 8/2010 | Orbay et al. |
| 2001/0037156 A1 | 11/2001 | Burstein et al. |
| 2002/0032446 A1 | 3/2002 | Orbay |
| 2002/0042654 A1 | 4/2002 | Masini |
| 2002/0045897 A1 | 4/2002 | Dixon et al. |
| 2002/0156474 A1 | 10/2002 | Wack et al. |
| 2003/0040753 A1 | 2/2003 | Daum et al. |
| 2003/0083667 A1 | 5/2003 | Ralph et al. |
| 2003/0171754 A1 | 9/2003 | Del Medico |
| 2003/0225411 A1 | 12/2003 | Miller |
| 2004/0034356 A1 | 2/2004 | LeHuec et al. |
| 2004/0097937 A1 | 5/2004 | Pike et al. |
| 2004/0102777 A1 | 5/2004 | Huebner |
| 2004/0102778 A1 | 5/2004 | Huebner et al. |
| 2004/0116930 A1 | 6/2004 | O'Driscoll et al. |
| 2004/0186482 A1 | 9/2004 | Kolb et al. |
| 2005/0011659 A1 | 1/2005 | Templeman et al. |
| 2005/0028398 A1 | 2/2005 | Jacobson |
| 2005/0049594 A1 | 3/2005 | Wack et al. |
| 2005/0049710 A1 | 3/2005 | O'Driscoll et al. |
| 2005/0086939 A1 | 4/2005 | Schmid |
| 2005/0090825 A1 | 4/2005 | Pfefferle et al. |
| 2005/0101961 A1 | 5/2005 | Huebner et al. |
| 2005/0165401 A1 | 7/2005 | Pack |
| 2005/0182406 A1 | 8/2005 | Orbay et al. |
| 2005/0187552 A1 | 8/2005 | Michelson |
| 2005/0216090 A1 | 9/2005 | O'Driscoll et al. |
| 2005/0234467 A1 | 10/2005 | Raines |
| 2005/0261688 A1 | 11/2005 | Grady, Jr. et al. |
| 2006/0089648 A1 | 4/2006 | Masini |
| 2006/0149265 A1 | 7/2006 | James et al. |
| 2006/0161158 A1 | 7/2006 | Orbay et al. |
| 2006/0173459 A1 | 8/2006 | Kay et al. |
| 2006/0195104 A1 | 8/2006 | Schlafli et al. |
| 2006/0200145 A1 | 9/2006 | Kay et al. |
| 2006/0264949 A1 | 11/2006 | Kohut et al. |
| 2007/0225714 A1 | 9/2007 | Gradl |
| 2007/0233111 A1 | 10/2007 | Orbay et al. |
| 2008/0009951 A1 | 1/2008 | Hodge |

FOREIGN PATENT DOCUMENTS

| | | |
|---|---|---|
| DE | 19936061 | 3/2000 |
| DE | 10015734 | 9/2001 |
| EP | 0471419 | 2/1992 |
| EP | 1836982 | 9/2007 |
| FR | 2367479 | 5/1978 |
| JP | 2003-102743 | 4/2003 |
| WO | WO99/05968 | 2/1999 |
| WO | WO01/91660 | 12/2001 |
| WO | WO03/007832 | 1/2003 |
| WO | WO2004/024009 | 3/2004 |
| WO | WO2004/045455 | 6/2004 |
| WO | WO 2004/084701 | 10/2004 |
| WO | WO2005020851 | 3/2005 |
| WO | WO2005023127 | 3/2005 |
| WO | WO2006065512 | 6/2006 |

OTHER PUBLICATIONS

The Distal Radius Plate Instrument and Implant Set Technique Guide; Synthes, 1995.

SCS/V Distal Radius Plate Volar; Avanta; 1998.
SCS/D Distal Radius Plate System; Avanta; 1997.
Sumary of Safety and Effectiveness Information; Synthes (USA); 1998.
Hand Innovations, DVR Anatomic Plate with F.A.S.T. Guide Technology, DVR Anatomic The Proven Standard in Volar Plating, on sale as of Mar. 2005.

U.S. Appl. No. 11/011,917, filed Dec. 14, 2004, Applicant: Javier E. Castaneda et al.
U.S. Appl. No. 12/977,705, filed Dec. 23, 2010, Applicant: Javier E. Castaneda et al.
U.S. Appl. No. 12/818,467, filed Jun. 18, 2010, Applicant: Jorge L. Orbay et al.
Graduated Stability Plates (GSP); Stryker Corporation; 2004.

BONE PLATE WITH PRE-ASSEMBLED DRILL GUIDE TIPS

RELATED CASES

This application is a continuation of U.S. Ser. No. 11/011,917, filed Dec. 14, 2004, issued as U.S. Pat. No. 8,172,886 on May 8, 21012, which is hereby incorporated by reference herein in its entirety.

BACKGROUND OF THE INVENTION

1. Field of the Invention

This invention relates broadly to surgical devices. More particularly, this invention relates to orthopedic implants, and specifically to bone plates and drill guides.

2. State of the Art

Fracture to the metaphysis of a long bone can be difficult to treat. Improper treatment can result in deformity and long-term discomfort.

By way of example, a Colles' fracture is a fracture resulting from compressive forces being placed on the distal radius, and which causes backward or dorsal displacement of the distal fragment and radial deviation of the hand at the wrist. Often, a Colles' fracture will result in multiple bone fragments which are movable and out of alignment relative to each other. If not properly treated, such fractures may result in permanent wrist deformity and limited articulation of the wrist. It is therefore important to align the fracture and fixate the bones relative to each other so that proper healing may occur.

Alignment and fixation of a metaphyseal fracture are typically performed by one of several methods: casting, external fixation, pinning, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Pinning with K-wires (Kirschner wires) is an invasive procedure whereby pins are positioned into the various fragments. This is a difficult and time consuming procedure that provides limited fixation if the bone is comminuted or osteoporotic.

Plating utilizes a stabilizing metal plate typically placed against the bone, fixed-angle pegs (which may have threaded or non-threaded shafts) positioned through the plate and entering drilled holes adjacent an articular bone surface, and cortical screws extending from the plate into holes drilled in the bone to provide stabilized fracture fixation. For example, co-owned U.S. Ser. No. 10/664,371, which is hereby incorporated by reference herein in its entirety, discloses a plate particularly adapted to treat dorsally displaced metaphyseal fractures from the volar side of the wrist.

When fixed-angle pegs are utilized in conjunction with a bone plate, it is necessary to ensure that the pilot holes drilled for the pegs are co-axial with the hole axes. Otherwise, the shaft of the pegs will not properly align with the anatomy, and the head of the pegs will not properly align with the threaded holes of the plate, potentially resulting in cross-threading. As a result, with the plate placed upon the bone, prior to drilling each hole in the bone in alignment with a peg hole, a drill guide is attached to the plate at the peg hole. The guide defines a tubular passage which directs the drill bit in the proper orientation for a peg through the particular peg hole. After drilling each hole, the drill guide is removed, the peg is inserted in the peg hole, and the drill guide is coupled to a subsequent peg hole.

The process of attaching the drill guide during the surgical procedure is laborious. It can be difficult to locate the appropriate angle for threadably coupling the guide to the peg hole during the procedure, given that each peg hole may have a discrete axis angle from the other peg holes. Such difficulty can unnecessarily prolong the surgical procedure.

SUMMARY OF THE INVENTION

It is therefore an object of the invention to provide facilitate the drilling of holes in bone in alignment with the peg holes in a bone plate.

It is another object of the invention to obviate the difficulties presented in connecting a drill guide in alignment with a hole in a bone plate at the time of surgery.

In accord with these objects, which will be discussed in detail below, drill guide tips are pre-assembled into at least one and preferably each of the threaded holes of the plate, so that surgeon does not have to thread the drill guide with the plate positioned on the bone. The pre-assembly can be done by the operating room technician or at the factory. The drill guide tips may be reusable or disposable. The tips are sufficiently short enough so that they do not interfere with adjacent tips or adjacent structure on the plate or intended to be inserted through the plate.

In a preferred method of pre-assembling the tips to the plate, a nest of short pins is placed beneath the plate such that the pins extend through the holes in the plate along the same angles as the axes of the holes. The pins then guide the tips to be thread into the holes at the correct angle. Alternatively, no nest is utilized and the tips are individually guided into the holes at the appropriate angle.

There are two options for using the tips. One is to attach a drill guide extension. The tip and extension together function as a conventional drill guide. After drilling, the extension is used to remove the tip from the plate. According to another use, the tip is used as a guide for a drill bit without any additional extension and then removed with a separate tool.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
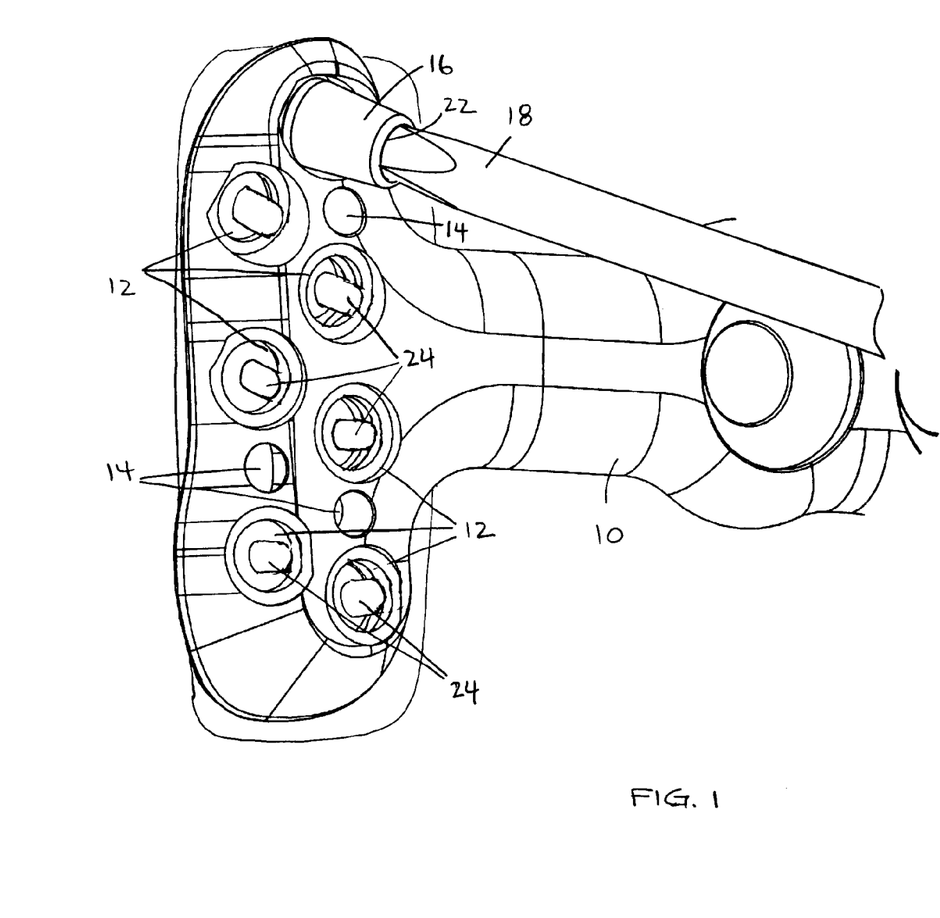
FIG. 1 is a perspective view of a bone plate and a drill guide tip being inserted or removed from the plate with a tool.
Figure 2:
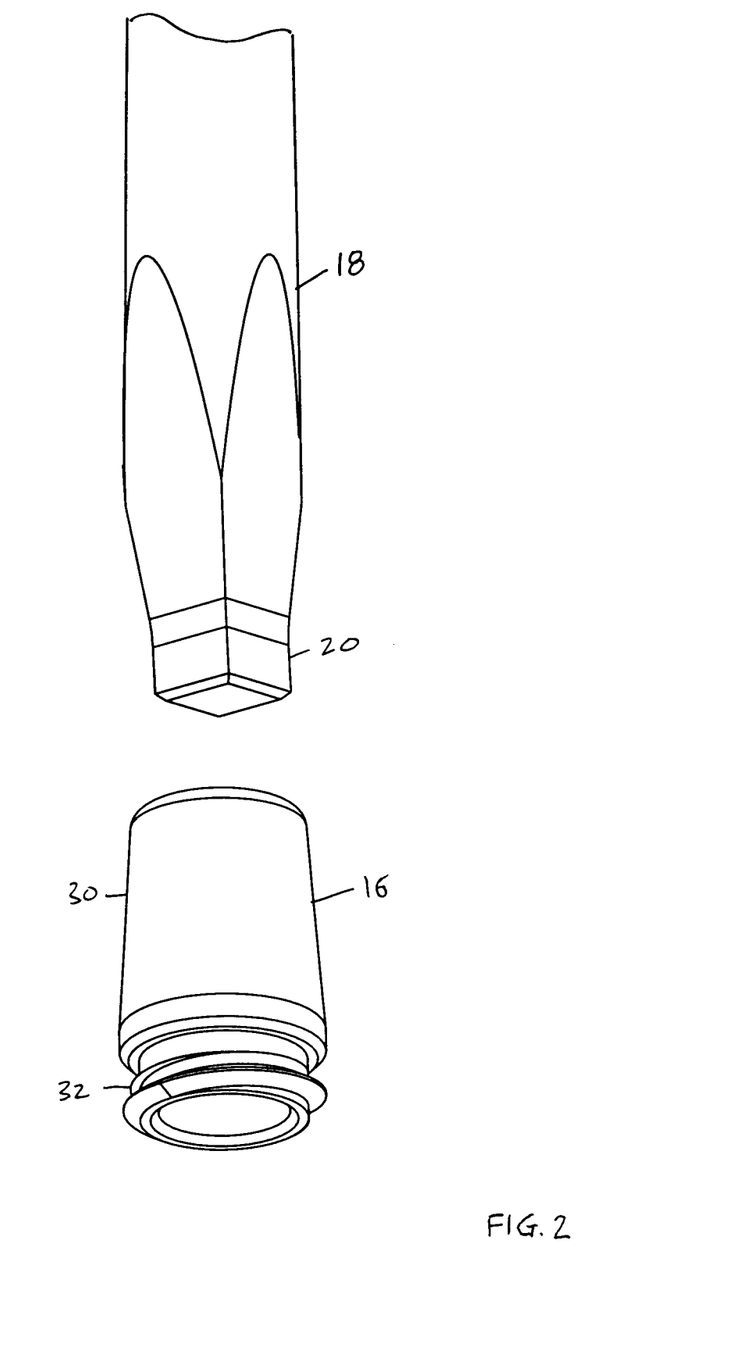
FIG. 2 is an exploded perspective view of drill guide tip and tool.

Turning now to FIG. 1, a bone plate 10 is shown. The bone plate shown is particularly for placement over the volar side of the distal radius. The bone plate 10 includes a plurality of threaded peg holes 12 for threadably receiving the heads of pegs or locking screws (not shown) therein and relatively smaller alignment holes 14 sized to closely receive K-wires in a fixed angle orientation. In a preferred bone plate, the axes of the peg holes are all oblique relative to each other. In one of the peg holes, a drill guide tip 16 is shown being pre-assembled into the hole with an insertion tool 18. Referring to FIGS. 1 and 2, in a preferred embodiment, the engagement between the insertion tool 18 and tip 16 is a tapered square 20 engaging a circular opening 22, with the edges of the square driver providing sufficient frictional force to rotate the tip into and out of engagement with the plate 10. Other suitable engagements may be used as well.

Pre-assembly of the tips 16 into the peg holes of the plate 10 is preferably performed so that surgeon does not have to thread the drill guide tips 16 with the plate once the plate 10 is positioned on the bone during the procedure. The pre-assembly can be done by the operating room technician or at the factory. In a preferred method of pre-assembly, a nest of short pins 24 is placed beneath the plate such that the pins extend through the holes in the plate along the same angles as the axes of the holes. The pins 24 then guide the tips to be thread into the holes at the correct angle. The pins 24 and insertion tool 18 are sized such that they do not interfere with each other. Alternatively, no nest is utilized and the tips 16 are individually guided into the holes at the appropriate angle. The drill guide tips 16 may be reusable or disposable.

Figure 3:
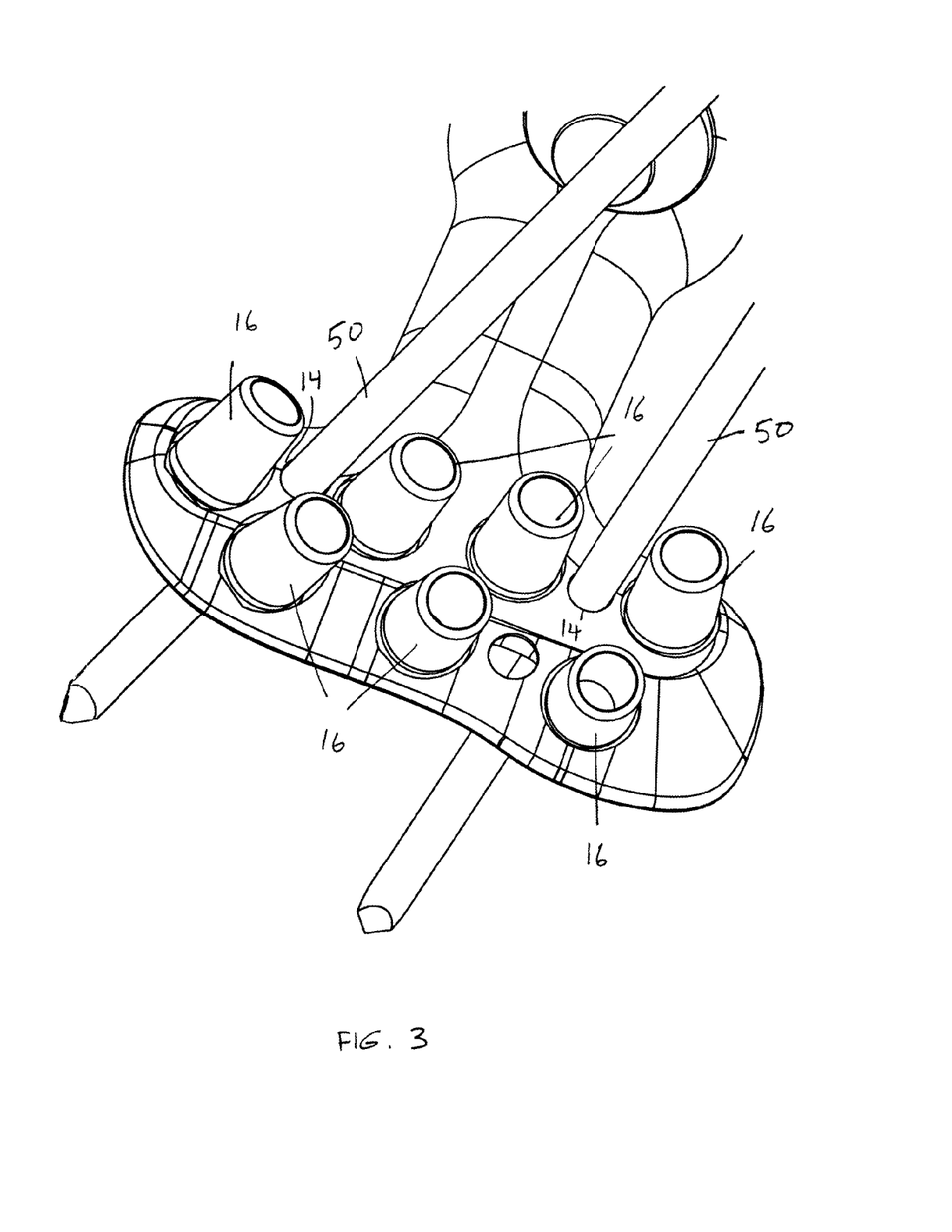
FIG. 3 is a perspective view of the bone plate loaded with drill guide tips and K-wires.

Referring to FIGS. 2 and 3, the tips 16 preferably have a frustoconically tapered upper portion 30 and lower threaded portion 32, and are sufficiently short so that they do not interfere with adjacent tips, adjacent structure on the plate, or structure intended to be inserted through the plate, e.g., K-wires 50 through alignment holes 14. The lower threaded portion 32 of the tips do not have to be as long as conventional drill guides, as the threading into the plate is done away from the surgical environment under easier conditions, whether at the factory (best case) or pre-implantation at the medical facility. Shortening the threaded portion reduces protrusion of the guide tip below the plate relative to convention drill guides, allowing the plate 10 to sit closer to the bone while drilling, as discussed further below.

The drill guide tips also eliminate the need to "countersink" holes for a drill guide for the distal row of holes in the plate. More particularly and for the following reasons, in the prior art it is initially necessary to drill holes in bone through the distal row of peg holes with a drill bit larger than the diameter of the peg shaft which will eventually be inserted through the peg holes. The plate is very thin at the distal row. The prior art drill guide has a "nose" section which is cylindrical and unthreaded and approximately 0.030" long, which is slightly longer than the pitch of the peg-hole thread (0.023"). The nose section diameter is just under the inner diameter of thread so that it guides itself with one full turn of the thread and establishes the direction of the hole before the threads are engaged. If the plate thread depth is very small (as is the case for distal holes) there is no room below the plate for the nose section of the drill guide because the bone block entry. Thus, countersink holes must be drilled.

Figure 4:
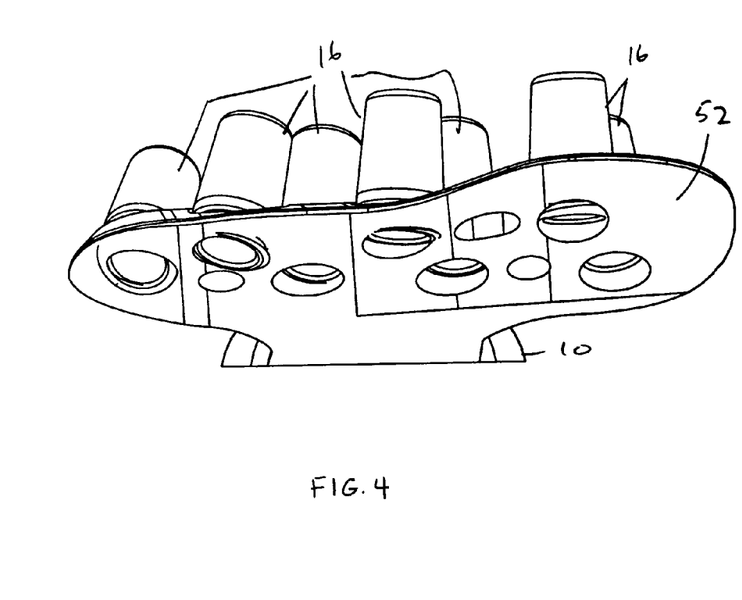
FIG. 4 is a front end view of a head portion of the plate showing that the drill guide tips do not protrude through the bottom surface of the plate.

In accord with the invention, the drill guide tips do not require a "nose" section since they will be assembled with some other guidance (e.g., the above described nest of pins 24) or freehand. The drill guide tips can be made very short since they need just to hold on to the threads of the peg holes. One and half threads of engagement has been shown to provide a satisfactory coupling of the tip to the plate, and referring to FIG. 4 provides that the drill guide tip 16 does not protrude through the bottom 52 of the plate 10. In addition to eliminating the requirement for countersinking, the fact that drill guide tips are so short results in the plate seating almost completely flush on the bone. Furthermore, the cylindrical unthreaded nose portion of the conventional drill guide, whose only job is to help the surgeon find by feel the current angle of the peg hole, is not required. A preferred size for each tip is preferably approximately 0.150-0.250 inch in length.

There are two options for using the tips. According to a first option, the tips 16 are used as the sole guide for a drill bit and then removed with a tool similar to the insertion tool 18. The length of the tips provides sufficient guidance for the drill bit. In this use, the inner surface of the tip is preferably hard, e.g., metal. Thus, the tips 16 may be made entirely of metal or have an outer plastic body with an insert molded metal tube, e.g. hypotube, which is hard and readily available with thin walls.

Figure 5:
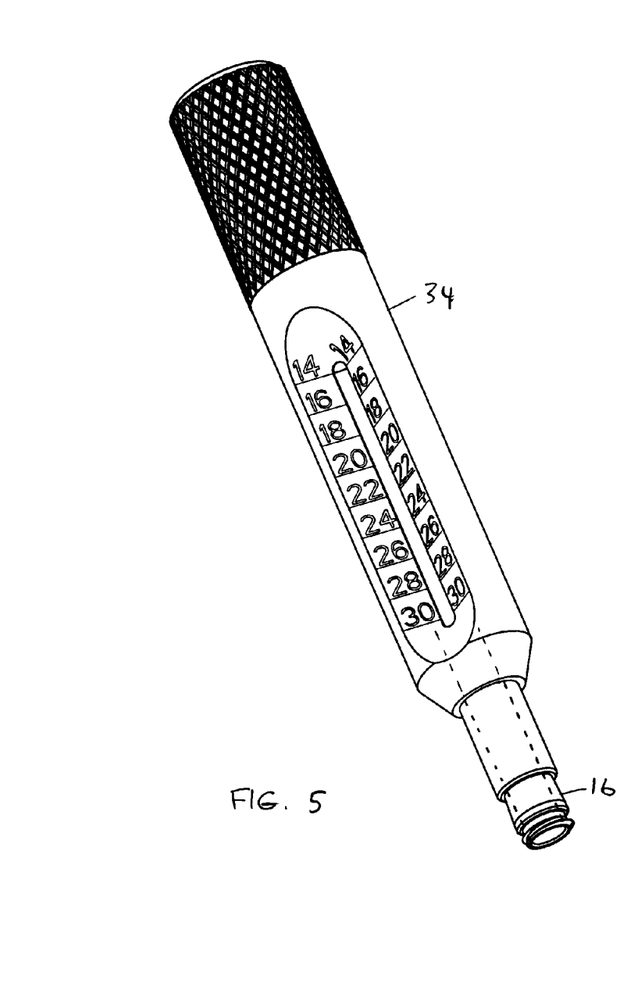
FIG. 5 is a perspective view of a drill guide tip and drill guide extension.

Referring to FIG. 5 and according to a second option, a drill guide extension 34 may be attached to the top of the tip 16. The tip 16 and extension 34 together function as a full length drill guide. The engagement between the drill guide extension 34 over the tip 16 is preferably such that a continuous constant diameter path is provided through the interiors of the extension and tip. To that end, the end 36 of the extension 34 is preferably stepped to fit the upper portion of the tip. The surgeon drills through the drill guide extension and tip, thereby taking advantage of the longer guidance which may be used in conjunction with a scale and/or gauge to measure the depth of the drilled hole for peg length selection. After drilling, the extension 34 and tip 16 are removed from the plate 10, and the extension 34 may also function as a tool for tip 16 removal. In fact, the taper at the upper portion 30 of the tip provides a means for axial and frictional engagement by the extension 34 which permits rotational engagement. Once removed from the plate, the tip is then is pulled of the extension by hand or may be dispensed into a container without manual contact.

It is desirable to have some provision within the surgical set to collect the tips for counting as they are removed; i.e., to ensure that all tips from the plate are removed from the surgical site. In order to facilitate collection of the tips, it is desirable that the drill guide tips have a very conspicuous color, e.g., green or blue. If made out of metal, it may be desirable to make them out titanium or aluminum and anodize them in a bright color that contrasts with the background in the surgical wound and the bone plate. A specialized container may be provided, or a dummy plate with threaded holes may be used to attach the tip thereto.

For drilling through the tips 16 where no drill guide extension is used, it may be desirable to modify the flutes of the drill bit, e.g. shortening and/or increasing twist, to reduce the play within the tip.

Figure 6:
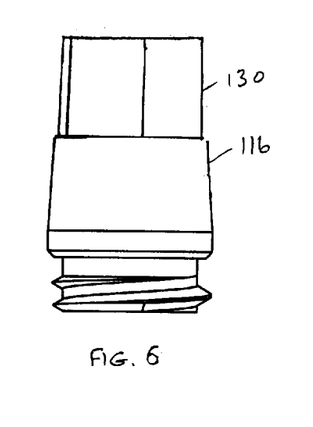
FIG. 6 is a side elevation of a first embodiment of a drill guide tip.
Figure 7:
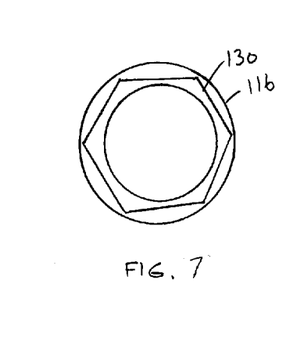
FIG. 7 is a top view of the first embodiment of the drill guide tip.
Figure 13:
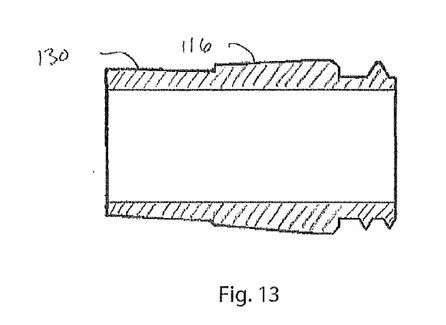
FIG. 13 is a longitudinal cross-section view through the embodiment shown in FIGS. 6 and 7.
Figure 14:
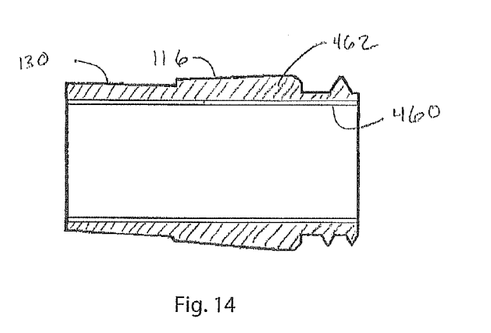
FIG. 14 is a longitudinal cross-section view of an alternate construction of the embodiment shown in FIGS. 6 and 7.

Other embodiments of the tips and extensions may be provided. For example, referring to FIGS. 6 and 7, the tips 116 may have an upper portion 130 with a exterior hex shape, or any non-circular exterior cross-sectional shape that will facilitate torque transmission. To remove the tip from the plate the surgeon rotates the extension, unthreading the tip. Such tips 116 may be formed of all metal as shown in FIG. 13 or may be a combination of a metal tube 460 and an outer plastic body 462 as shown in FIG. 14.

Figure 8:
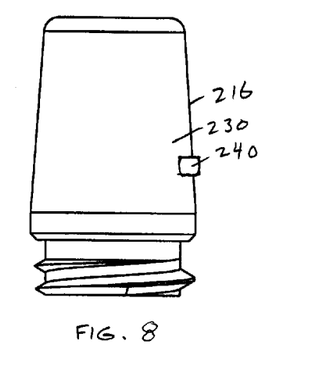
FIG. 8 is a side elevation of a second embodiment of a drill guide tip.
Figure 9:
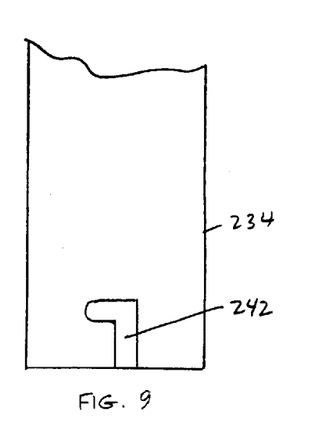
FIG. 9 is a side elevation view of an embodiment of drill guide extension.
Figure 15:
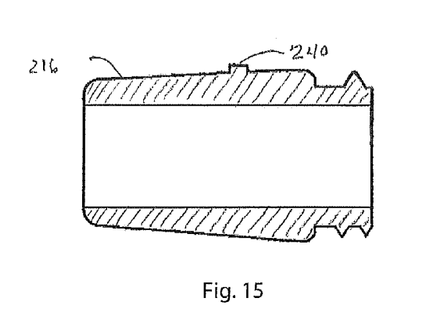
FIG. 15 is a longitudinal cross-section view through the embodiment shown in FIGS. 8 and 9.
Figure 16:
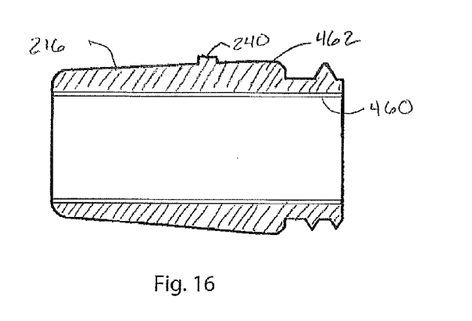
FIG. 16 is a longitudinal cross-section view of an alternate construction of the embodiment shown in FIGS. 8 and 9.

Turning now to FIGS. 8 and 9, according to another embodiment of the invention, the tips 216 may be joined to the extension via one or more lateral protrusions 240 on the body 230 of the tip and corresponding "key slots" 242 in the extension 234. Such tips 216 may be formed of all metal as shown in FIG. 15 or may be a combination of a metal tube 460 and an outer plastic body 462 as shown in FIG. 16.

Figure 10:
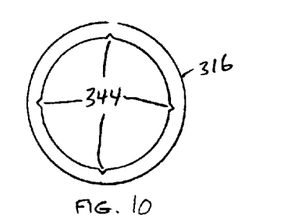
FIG. 10 is a top view of a third embodiment of a drill guide tip.

Referring to FIG. 10, according to a further embodiment of the invention, the tips 316 may be joined to the extension by providing one or more corners 344 to the inner circular opening 322 of the tip, and one or more outer corresponding corners on the extension which frictionally engage in the tip.

Figure 11:
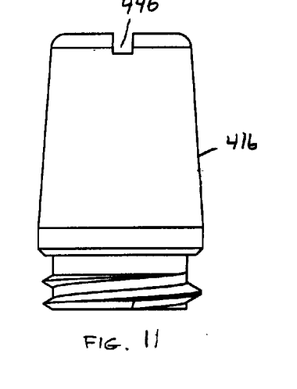
FIG. 11 is a side elevation of a fourth embodiment of a drill guide tip.
Figure 12:
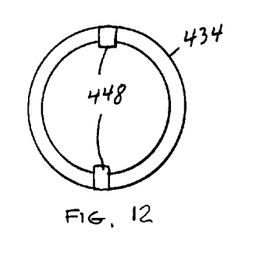
FIG. 12 is a bottom view of an embodiment of a drill guide extension engageable with the drill guide tip of FIG. 11.
Figure 17:
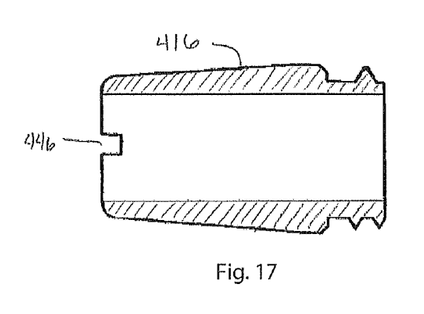
FIG. 17 is a longitudinal cross-section view through the embodiment shown in FIGS. 11 and 12.
Figure 18:
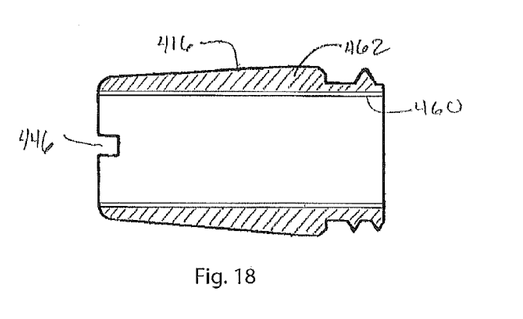
FIG. 18 is a longitudinal cross-section view of an alternate construction of the embodiment shown in FIGS. 11 and 12.

Turning to FIGS. 11 and 12, according to another embodiment of the invention, the tips 416 may include an upper radially arranged slots 446 (e.g., 180° or 120° separation) and the extension 434 includes corresponding radially arranged pegs 448 which engage the tips 416 at the slots 46. Such tips 416 may be formed of all metal as shown in FIG. 17 or may be a combination of a metal tube 460 and an outer plastic body 462 as shown in FIG. 18.

There have been described and illustrated herein several embodiments of a bone plate with pre-assembled drill guide tips and methods of using the same. While particular embodiments of the invention have been described, it is not intended that the invention be limited thereto, as it is intended that the invention be as broad in scope as the art will allow and that the specification be read likewise. Thus, while the tips have been shown with respect to a volar plate for dorsally displaced fractures, it will be appreciated that the tips may be used for threaded holes on other bone plates as well. In addition, while particular engagements between the tips and the insertion/removal tool and the tips and drill guide extension have been disclosed, it will be understood that other suitable engagements can also be used. Also, while the drill guide tips are described as threaded into the peg holes, it is appreciated that non-threaded assemblies which maintain the tips in alignment with the axes of the peg holes can also be used. It will therefore be appreciated by those skilled in the art that yet other modifications could be made to the provided invention without deviating from its spirit and scope as claimed.

What is claimed is:

1. A bone plate system for use in fixation of a fractured bone, said system comprising:
    a) a bone plate for placement on the bone, said bone plate including an elongate shaft-like body and a head oriented transverse to said body,
    said head having a plurality a threaded first holes for receiving and retaining the heads of first fasteners in threaded engagement with said threaded first holes, said threaded first holes defining respective fixed holes axes,
    said shaft having a plurality a second holes longitudinally displaced along said shaft for receiving second fasteners therethrough, and
    said plate including a bone contacting first surface, an opposite second surface, and a thickness extending in a dimension between said first and second surfaces; and
    b) a plurality of removable tubular drill guide tips threadedly engaged within said plurality of threaded first holes of said bone plate in axial alignment with said fixed hole axes,
    each drill guide tip having an internal surface defining a bore, a proximal guiding end, an externally threaded distal end for engagement with said threaded holes, and a longitudinal axis extending through a radial center of said bore,
    said drill guide tip having a body portion extending between said guiding end and said plate, said body portion having a length that extends above said second surface of said bone plate by more than said thickness of said bone plate, yet said length is sufficiently short so that said body portion does not interfere with a body portion of an adjacent drill guide tip, said body portion having an external surface defining a non-circular cross-sectional shape transverse to said longitudinal axis.

2. A bone plate system according to claim 1, wherein: said head is angled out of plane relative to said body.

3. A bone plate system according to claim 1, wherein: said second holes are larger than said first holes.

4. A bone plate system according to claim 1, wherein: said second holes are non-threaded.

5. A bone plate system according to claim 1, wherein: said plurality of first threaded holes includes at least three threaded holes, each of which is threadedly engaged by one of said tubular drill guide tips.

6. A bone plate system according to claim 1, wherein: said body portion of said tubular drill guide is tapered.

7. A bone plate system according to claim 1, wherein: said body portion of said tubular drill guide includes a conically tapered portion.

8. A bone plate system according to claim 1, wherein: said body portion of said tubular drill guide includes an external surface defining a non-circular shape in cross-section transverse to a longitudinal axis through said bore of said drill guide tip.

9. A bone plate system according to claim 8, wherein: said non-circular shape is a hexagon.

10. A bone plate system according to claim 1, wherein: said non-circular shape is defined along only a portion of said body portion.

11. A bone plate system according to claim 1, wherein: said body portion of said drill guide tip does not exceed 0.25 inch in length.

12. A bone plate system for use in fixation of a fracture of a distal radius bone, the distal radius bone having a volar side and a dorsal side, said system comprising:
    a) a bone plate for placement over the volar side of the distal radius, said bone plate including an elongate shaft-like body and a head oriented transverse to said body, said head having a plurality a threaded first holes for receiving and retaining the heads of first fasteners in threaded engagement with said threaded first holes, said threaded first holes defining respective fixed holes axes, said shaft having a plurality a second holes longitudinally displaced along said shaft for receiving second fasteners therethrough, and said head angled out of plane relative to said body, said plate including a bone contacting first surface, an opposite second surface, and a thickness extending in a dimension between said first and second surfaces; and b) a plurality of removable tubular drill guide tips threadedly engaged within said plurality of threaded first holes of said bone plate in axial alignment with said fixed hole axes, each drill guide tip having an internal surface defining a bore, a proximal guiding end, an externally threaded distal end for engagement with said threaded holes, and a longitudinal axis extending through a radial center of said bore, said drill guide tip having a body portion extending between said guiding end and said plate, said body portion having a length that extends above said second surface of said bone plate by more than said thickness of said bone plate, yet said length is sufficiently short so that said body portion does not interfere with a body portion of an adjacent drill guide tip, said body portion having an external surface defining a non-circular cross-sectional shape transverse to said longitudinal axis.

13. A bone plate system according to claim 12, wherein: said plurality of threaded first holes includes a proximal row of first holes and a distal row of first holes, each of which is threadedly engaged by one of said tubular drill guide tips.

14. A bone plate system according to claim 12, wherein: said distal row of first holes is provided in a distally tapered portion of said head.

15. A bone plate system according to claim 12, wherein: said second holes are larger than said first holes.

16. A bone plate system according to claim 12, wherein: said second holes are non-threaded.

17. A bone plate system according to claim 12, wherein: said plurality of first threaded holes includes at least three threaded holes, each of which is threadedly engaged by one of said tubular drill guide tips.

18. A bone plate system according to claim 12, wherein: said body portion of said tubular drill guide is tapered.

19. A bone plate system according to claim 12, wherein: said body portion of said tubular drill guide includes a conically tapered portion.

20. A bone plate system according to claim 12, wherein: said body portion of said tubular drill guide includes an external surface defining a non-circular shape in cross-section transverse to a longitudinal axis through said bore of said drill guide tip.

21. A bone plate system according to claim 20, wherein: said non-circular shape is a hexagon.

22. A bone plate system according to claim 20, wherein: said non-circular shape is defined along only a portion of said body portion.

23. A bone plate system according to claim 12, wherein: said body portion of said drill guide tip does not exceed 0.25 inch in length.

* * * * *